United States Patent [19]

Saville

[11] Patent Number: Plant 6,876

[45] Date of Patent: Jun. 27, 1989

[54] ROSE PLANT NAMED SAVACLOUD

[75] Inventor: F. Harmon Saville, Rowley, Mass.

[73] Assignee: Nor'East Miniature Roses, Inc., Rowley, Mass.

[21] Appl. No.: 174,972

[22] Filed: Mar. 29, 1988

[51] Int. Cl.[4] ..... A01H 5/00

[52] U.S. Cl. ..... Plt./9

[58] Field of Search ..... Plt./9

*Primary Examiner*—Robert E. Bagwill
*Attorney, Agent, or Firm*—Vincent G. Gioia

[57] ABSTRACT

A new miniature rose variety which is near white with a pink cast.

1 Drawing Sheet

The present invention relates to a new and distinct variety of rose plant of the miniature rose class, which is a flower color mutation (sport) of the miniature rose known as "Buttons and Bows" (U.S. Plant Pat. No. 4,939) that I discovered in my greenhouse. The varietal denomination of the new variety is "Savacloud".

Among the novel characteristics possessed by this new variety which distinguish it from its parent and all other varieties of which I am aware are its attractive coloring which is near white with a pink cast with deeper pink hue where petals bunch and which are long lasting on the plant and after cutting. The plant is very vigorous and disease resistant. Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "56D", is plate 56D of The Royal Horticultural Society Colour Chart.

Parentage: Mutation of the miniature rose known as "Buttons and Bows".
Class: Miniature.

The following observations are made of specimens grown under glass in San Bernardino County, Calif. during the month of January.

FLOWER

Blooming habit: Continuous.

A. Bud:
- (1) *Size.*—Medium.
- (2) *Form.*—Ovate.
- (3) *Color.*—After sepals fall, near 56D to 56C.
- (4) *Sepals.*—Simple, acuminate, longer than bud, pilose inside, glabrous outside.

- (5) *Peduncle.*—Length — about 1 to 1½ inch. Aspect — straight. Strength — erect. Color — near 143C.

B. Bloom:
- (1) *Size.*—Average size when fully expanded — about 1½ inch.
- (2) *Borne.*—Singly and sprays of 3 to 4 blooms.
- (3) *Form.*—Cupped, high centered, reflexing at maturity.
- (4) *Petalage.*—Number of petals under normal conditions — about 25 to 30.
- (5) *Color.*—As buds open, outer petals's top surface visible is near 56D in coloring; that is, near white with a pink cast. But where petals remain bunched, color is a deeper pink hue, near 56C to 56D. As petals unfurl, pink tonality remains visible toward flower centers but petals are lighter toned, especially at petal top surfaces. Petal undersurfaces retain pink cast resembling the coloring of bunched inner petals. When flowers are fully open, they reveal yellow flower centers, near 16C, which contrast very attractively with pink cast, near white flower petals. Flowers whiten upon aging.

C. Petals:
- (1) *Texture.*—Relatively thick.
- (2) *Appearance.*—Inside velvety, outside satiny.
- (3) *Form.*—Fan shaped usually rounded at outer edges, sometimes reflexing to a point, sometimes folding under.
- (4) *Arrangement.*—Regularly arranged, shingle-like.
- (5) *Petaloids in Center.*—Few.
- (6) *Persistence.*—Drop off cleanly.
- (7) *Fragrance.*—Slight.
- (8) *Lasting quality.*—Long lasting on plant and as cut flower.

REPRODUCTIVE ORGANS

A. Stamens, filaments and anthers:
- (1) *Arrangement.*—Regular, outer stamens curved.
- (2) *Color.*—Near 16C.

B. Pollen:
- *Color.*—Near 16A.

C. Styles: Few, medium length, even, tightly bunched.

D. Stigmas:
- *Color.*—Near 8D.

E. Hips: None observed.

PLANT

A. Form: Upright.

B. Growth: Vigorous, uniform.

*Height attained.*—About 14 to 16 inches.

C. Foliage: Compound.

(1) *Size.*—Medium.

(2) *Quantity.*—Abundant, close set.

(3) *Color.*—Upper side — near to 137B. Under side — near to 137B.

(4) *Shape.*—Oval, acuminate.

(5) *Texture.*—Upper side is shiny and under side is satiny.

(6) *Edge.*—Serrated.

(7) *Serration.*—Simple.

(8) *Leaf stem.*—Color — near to 146C. Under side — near 146C.

(9) *Stipules.*—Short, broad, pointed.

(10) *Resistance to disease.*—Blackspot — Excellent. Mildew — Excellent. Rust — Excellent.

D. Wood:

(1) *New wood.*—Color — near 143C. Bark — smooth.

(2) *Old wood.*—Color — near 144A. Bark — smooth.

E. Thorns:

(1) *Thorns.*—Quantity (main stalk) — many, scattered. On laterals from stalk — few. Form — straight, pointed. Length — medium. Color — near 51A. Position — scattered.

(2) *Prickles.*—None.

F. Winter hardiness: Very hardy.

I claim:

1. A new and distinct variety of rose plant of the miniature rose class, substantially as shown and described, characterized particularly by very attractive near white flowers with a pink cast and which are long lasting on the plant and after cutting and are borne on a vigorous disease resistant plant.

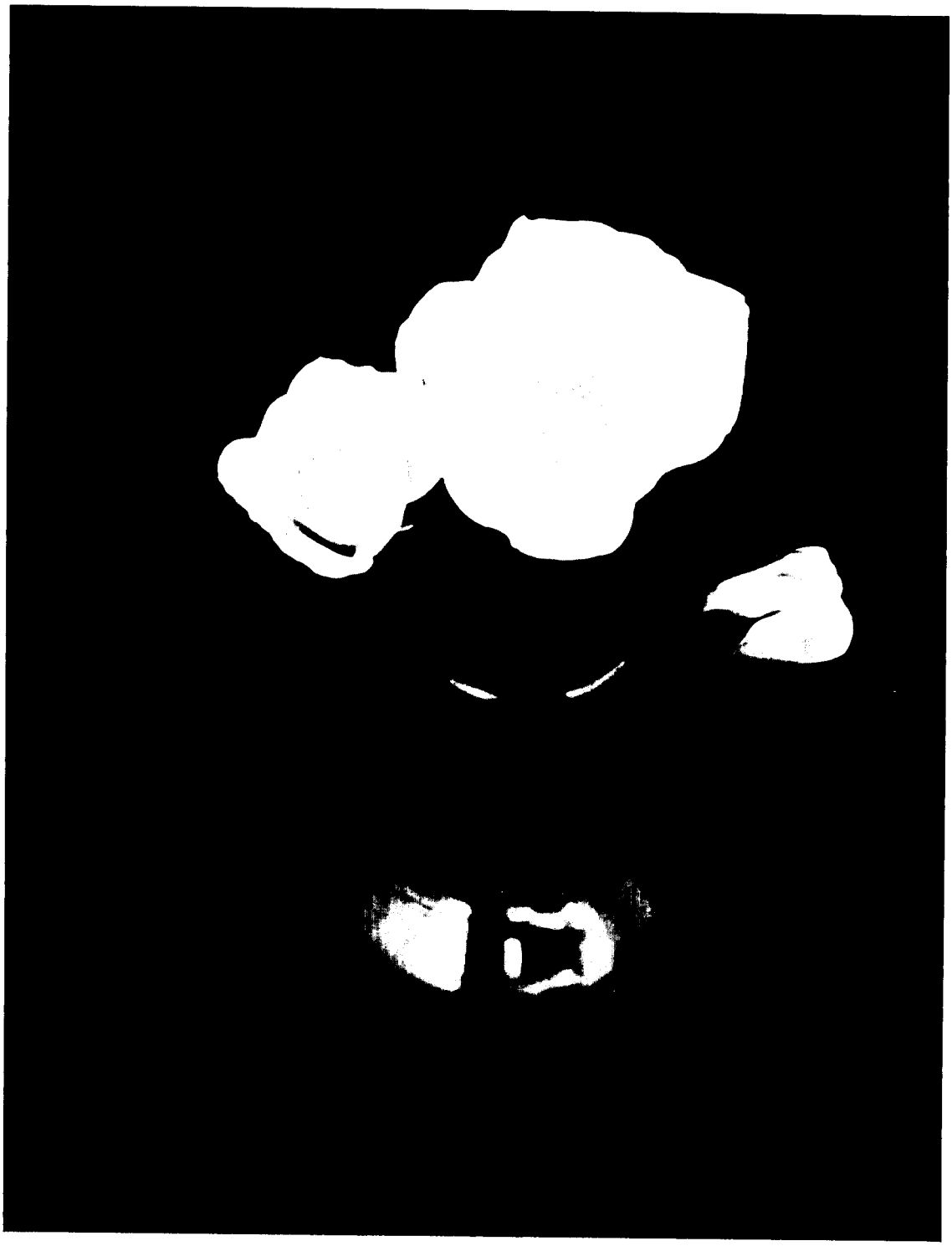

* * * * *